United States Patent [19]

Lorenz

[11] Patent Number: 4,933,884
[45] Date of Patent: Jun. 12, 1990

[54] METHOD OF AND APPARATUS FOR DETERMINING THRESHOLD VALUES FOR THE ANALYSIS OF PARTICLES CONTAINED IN A LIQUID

[75] Inventor: Adrian Lorenz, Zürich, Switzerland
[73] Assignee: Contraves AG, Zürich, Switzerland
[21] Appl. No.: 151,215
[22] Filed: Feb. 1, 1988

[30] Foreign Application Priority Data

Feb. 5, 1987 [CH] Switzerland .................. 00411/87

[51] Int. Cl.⁵ .................................. G01N 27/00
[52] U.S. Cl. ........................ 364/555; 364/413.07; 377/11; 436/63
[58] Field of Search .................. 364/555, 556, 413.07, 364/413.08, 413.11; 73/861.41; 377/1 D, 11, 12; 356/39, 442; 436/63; 250/576

[56] References Cited

U.S. PATENT DOCUMENTS

| 3,973,725 | 8/1976 | Watanabe et al. ............ 364/555 X |
| 4,309,757 | 6/1980 | Frey et al. ..................... 364/555 |
| 4,314,346 | 2/1982 | Frier et al. ................ 364/413.07 X |
| 4,453,226 | 6/1984 | Hobbs et al. ................... 364/555 |
| 4,656,139 | 4/1987 | Matsuda et al. ............. 436/63 X |
| 4,667,335 | 5/1987 | Deindoerfer .................... 377/10 |
| 4,706,207 | 11/1987 | Hennessy et al. .............. 364/555 |
| 4,727,020 | 2/1988 | Recktenwald ................ 436/63 X |

FOREIGN PATENT DOCUMENTS

0012418  6/1980  European Pat. Off. .

OTHER PUBLICATIONS

Valtonen, N. K. "The Cell Spectrometer: An Apparatus for the Semi-Automatic Determination of the Volume Distributions of Blood Cells", *Biomedical Engineering*, vol. 8, No. 9, Sep. 1973, pp. 384–389.
Computer Graphics and Image Processing, vol. 7, No. 2, Apr. 1978, pp. 259–265, New York, U.S.A., Article of J. S. Weszka, and entitled: "A Survey of Threshold Selection Techniques".

Primary Examiner—Parshotam S. Lall
Assistant Examiner—Joseph L. Dixon
Attorney, Agent, or Firm—Werner Kleeman

[57] ABSTRACT

The apparatus for analyzing particles in a particle containing fluid, especially pretreated liquids containing blood samples, contains storage devices and computing sections for determining separation threshold values and the particle distribution as a function of a predetermined particle parameter. The separation threshold values are determined on the basis of measured values of the predetermined particle parameter arranged in individual histograms containing at least two particle population maxima and minima. At least one particle population minimum is determined using an adaptive method. For insufficiently distinct particle population minima, there is first determined, on the basis of histograms containing corresponding distinct particle population minima and maxima, a characteristic difference quotient:

$$Q_x(j,k)_{res} = \frac{\text{Min.}(x) - \text{Min.}(j)}{\text{Max.}(k) - \text{Min.}(j)}$$

The separation threshold value associated with the insufficiently distinct particle population minimum is determined on the basis of the characteristic difference quotient according to:

$S_x(j,k)_{unres} = $
$(\text{Max.}(k) - \text{Min.}(j))_{unres} \cdot Q_x(j,k)_{res} + \text{Min.}(j)_{unres}$ 27 Claims, 2 Drawing Sheets

METHOD OF AND APPARATUS FOR DETERMINING THRESHOLD VALUES FOR THE ANALYSIS OF PARTICLES CONTAINED IN A LIQUID

CROSS-REFERENCE TO RELATED PATENTS

This application is related to (i) the commonly assigned U.S. Pat. No. 4,309,757, granted Jan. 5, 1982, entitled "METHOD FOR CLASSIFICATION OF SIGNALS BY COMPARISON WITH AN AUTOMATICALLY DETERMINED THRESHOLD", and (ii) the commonly assigned U.S. Pat. No. 4,314,346, granted Feb. 2, 1982, and entitled "AUXILIARY APPARATUS FOR A PARTICLE ANALYZER". The disclosures of these patents is incorporated herein by reference.

BACKGROUND OF THE INVENTION

The present invention relates to a method of, and apparatus for, analyzing particles dispersed in a fluid, especially a liquid containing a blood sample.

In its more particular aspects, the present invention specifically relates to a method of, and an apparatus for, analyzing particles dispersed in a fluid and which apparatus comprises first storage means as well as a first computing section and a second computing section for determining separation threshold values which are utilized for the particle analysis in the fluid, particularly the liquid containing the blood sample. Such separation threshold values are determined on the basis of measured values of a predetermined particle parameter and the number of particles which are associated with the measured values and are dispersed in the particle containing fluid. The predetermined particle parameter, for example, may constitute the size or volume of the analyzed particles such as, for example, blood cells in a blood containing liquid sample.

The measured values are arranged in the form of individual histograms which are related to individual samples of the particle containing fluid. Each one of the individual histograms contains at least two particle population maxima and at least two particle population minima. At least one of the at least two particle population minima is determined using conventional adaptive techniques.

Each individual sample of the particle containing fluid or fluid mixture, especially a liquid containing a blood sample, contains particles of different species or classes which differ with respect to, for example, the particle size or volume. Such different species or classes of particles are present in different samples of the particle containing fluid in corresponding different particle distributions or particle distribution densities. Such different particle distributions or particle distribution densities are expressed by the different particle population maxima in the aforementioned individual histograms. Consequently, during the particle analysis of a particle containing fluid or fluid mixture, especially a liquid containing a blood sample, there is required a differentiation between the different particle distributions or particle distribution densities of the various particle species or particle populations. This differentiation is effected by analyzing the individual histograms utilizing so-called separation threshold values. Such separation threshold values can also be utilized to differentiate or discriminate between overlapping particle distributions or particle distribution densities of the various species or populations. In any case, the separation threshold values are set at predetermined particle population minima such as to permit substantially error-free evaluation of the individual histograms in terms of the different particle populations.

Multifarious criteria exist for setting the aforementioned separation threshold values in the individual histograms or particle distributions which are obtained as the result of the measurement of the aforementioned measured values of the predetermined particle parameter and the number of particles which are associated with such measured values. In accordance with corresponding criteria there can be differentiated in principle between fixedly set separation threshold values and adaptive separation threshold values which "follow" the particle populations in the individual histograms. The method and apparatus according to the present invention can be used with both types of separation threshold values. Most preferred, however, is the utilization of the present invention in conjunction with adaptive separation threshold values.

In an apparatus such as known, for example, from European Patent Publication No. 0,012,418, published June 25, 1980, cognate with the aforementioned U.S. Pat. No. 4,309,757, granted Jan. 5, 1982, there can be analyzed, for example, a correspondingly prepared liquid containing a blood sample for erythrocytes. The apparatus carries out appropriate operations or steps and contains appropriate means for automatically, i.e. adaptively finding the separation threshold value associated with a particle population minimum in the histogram which is obtained as a result of the investigation of the liquid containing the blood sample which contains a bimodal distribution of the particle size. Such adaptively determined separation threshold value which is associated with a related particle population minimum in the individual histogram, permits discriminating or differentiating between overlapping size or volume distributions of the particles contained in the particle containing fluid sample.

Multimodal distributions containing overlapping particle populations show markedly differently distinct or resolved particle population maxima and particle population minima. Practically, the particle population minima exclusively serve as a criterium for the separation or resolution between two overlapping particle populations. Generally, the particle population maxima are not used as separation or resolution or differentiation criteria. Frequently, however, the desired particle population minima are insufficiently distinctly formed or resolved and, as a consequence, the detection or location of a suitable separation threshold value already fails solely for the reason of such insufficient resolution.

Thus, for example, with liquids containing blood samples having relatively small lymphocyte concentrations, there exists the problem that the desired particle population minima frequently are insufficiently distinct or resolved whereby the detection or setting of a useful separation threshold value is not ensured.

SUMMARY OF THE INVENTION

Therefore, with the foregoing in mind it is a primary object of the present invention to provide a new and improved method of, and apparatus for, analyzing particles dispersed in a fluid and which method and apparatus are not afflicted with the aforementioned drawbacks and limitations of the prior art.

A further significant object of the present invention is directed to providing a new and improved method of, and apparatus for, analyzing particles dispersed in a fluid and which method and apparatus permit determining separation threshold values in the presence of insufficiently distinct or resolved particle population minima.

The invention is based on an interesting observation which has been made during particle analysis for determining blood cells and relates to a specific property of the histograms showing bimodal or multimodal particle distributions. This observation has been affirmed in numerous experiments and can be summarized as follows:

A characteristic predetermined difference quotient Q can be formed from (i) the difference between the measured values of the predetermined particle parameter at the location of a particle population minimum x and a particle population minimum j; and (ii) the difference between the measured values of the predetermined particle parameter at the location of a particle population maximum k which is associated with the particle population minimum x, and the aforementioned particle population minimum j.

The quotient formed by the two aforementioned differences was found to be approximately constant and independent of the type of preparation or pretreatment of the sample which was used for the blood cell analysis. Thus, within a predetermined series of samples, the knowledge of the characteristic predetermined difference quotient Q enables determining in an individual histogram, on the basis of the location of a sufficiently distinct or resolved particle population minimum and the location of the associated particle population maximum, the location of a particle population minimum which can not be sufficiently exactly detected or determined in such individual histogram. Consequently, there can thus be determined also with sufficient precision the insufficiently defined separation threshold value S which is associated with such insufficiently distinct or resolved particle population minimum.

For instance, when a mixed distribution of three cell populations of white blood cells is chemically prepared or processed in different manners, there will correspondingly vary the volumina associated with the three particle populations and also the locations of the separation threshold values which are associated with the particle population minima. However, the mutual relationship between the particle population maxima and the particle population minima remains almost invariant. Based on this observation there resulted the concept of using such "regularity" or relationship in all those cases in which there fail the known methods of determining the separation threshold values and the related criteria. In this context "fail" should be understood to mean that the known methods for determining threshold separation values may detect some but do not detect all of the separation threshold values which have to be determined. The inventive method and apparatus thus become effective in those cases in which the known methods and apparatuses fail and, in fact, are complementary thereto and eliminate the deficiencies of the known methods and apparatuses. As a result, the inventive method and apparatus have a much higher efficiency in comparison to conventional methods and apparatuses for determining the aforementioned separation threshold values.

Now in order to implement these and still further objects of the present invention, which will become more readily apparent as the description proceeds, the method of the present development is manifested by the features that, (a) at least one characteristic predetermined difference quotient is from each individual histogram utilizing corresponding particle population minima and particle population maxima;

(b) the characteristic predetermined different quotients related to predetermined insufficiently defined separation threshold values, are ordered and stored and mean values are formed of such characteristic predetermined difference quotients;

(c) the characteristic predetermined difference quotient is selected for each insufficiently defined separation threshold value to be fixed or determined;

(d) the stored characteristic predetermined difference quotients are checked for the presence of a characteristic predetermined difference quotient which is related to the separated threshold value to be fixed or determined with respect to an individual histogram and, in the absence of such characteristic predetermined difference quotient, the individual histogram is stored;

(e) the individual insufficiently defined separation threshold values are determined on the basis of the particle population minima and the particle population maxima as well as the determined characteristic predetermined difference quotients, the thus determined separation threshold values are checked with respect to predetermined boundary conditions and, if such boundary conditions are satisfied, are utilized for determining particle distributions as a function of the predetermined particle parameter;

(f) individual histograms are stored in those cases in which no characteristic predetermined difference quotient could be determined; and (g) non-analyzable histograms containing insufficiently defined separation threshold values are detected and their presence is signalled to the operator of the apparatus or to a correspondingly devised unit of the apparatus.

As alluded to above, the invention is not only concerned with the aforementioned method aspects, but also relates to a novel construction of apparatus for carrying out the same. Generally speaking, the inventive apparatus comprises an apparatus for analyzing particles contained in a fluid.

To achieve the aforementioned measures, the inventive apparatus, in its more specific aspects, comprises apart from the initially noted structure:

a third computing section containing means for determining a predetermined number of characteristic predetermined difference quotients, means for selecting at least one of said predetermined number of characteristic predetermined difference quotients for at least one separation threshold value to be fixed, means for checking the presence of an appropriate characteristic predetermined difference quotient, and means for storing histograms in the absence of related characteristic predetermined difference quotients;

second storage means for ordering and storing characteristic predetermined difference quotients which are related to predetermined separation threshold values, and forming mean values of such characteristic predetermined difference quotients;

a fourth computing section containing means for determining a predetermined number of insufficiently defined separation threshold values, means for checking at least one separation threshold value which is determined on the basis of at least one related characteristic predetermined difference quotient, with respect to boundary conditions required for determining the particle distribution as a function of the predetermined particle parameter; and third storage means for storing histograms in the absence of related characteristic predetermined difference quotients and containing means for utilizing such histograms at a later time during the particle analysis.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings, there have been generally used the same reference characters to denote the same or analogous components and wherein.

DETAILED DESCRIPTION OF THE PREFERRED EMBODIMENTS

Describing now the drawings, it is to be understood that only enough of the construction of the inventive apparatus has been shown as is needed to enable a person skilled in the art to readily understand the underlying principles and concepts of the present development, while simplifying the showing of the drawings.

Figure 1:
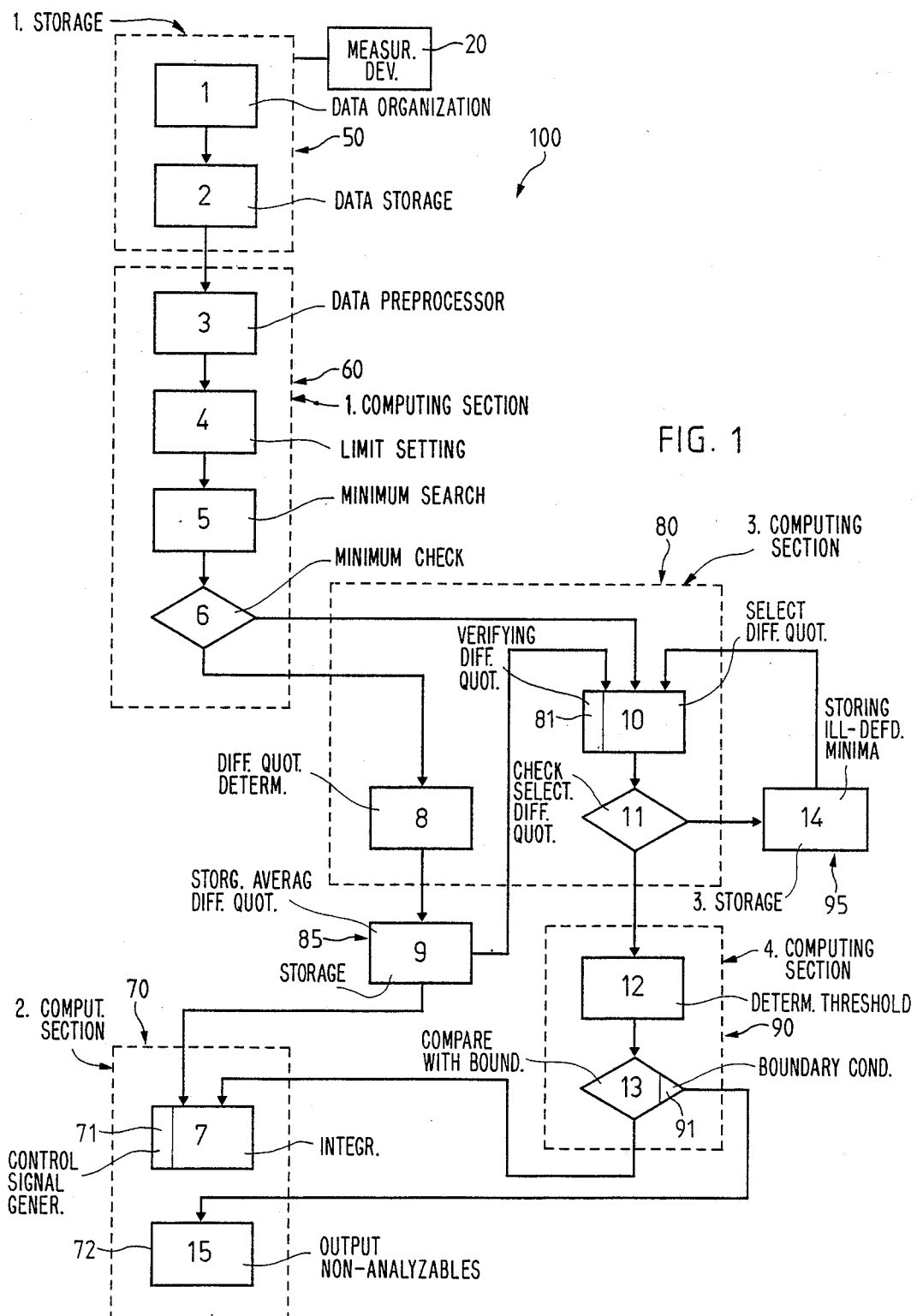
FIG. 1 is a schematic block circuit diagram of an exemplary embodiment of the inventive apparatus.

Turning now specifically to FIG. 1 of the drawings, the inventive apparatus 100 illustrated therein by way of example and not limitation will be seen to comprise a measuring device 20 for analyzing the particles contained in individual samples of a predetermined number of samples of a particle containing fluid which, for example, may constitute an appropriately prepared liquid containing a blood sample. The measuring device 20 contains a conventional detection zone and the individual samples are passed through such detection zone. Appropriately selected electrically and/or optically operating detection means are associated with the detection zone so that, during the passage of each individual sample through the detection zone, the particles dispersed in each individual sample are scanned by the electrically and/or optically operating detection means. The electrically and/or optically operating detection means respond to the particles which are passed through the detection zone, and generate pulses or signals which correspond to a predetermined particle parameter like, for example, the size or volume of the particles. Simultaneously, the number of particles is counted which are associated with the aforementioned pulses or signals generated by the electrically and/or optically operating detection means.

Although, in the description herein to follow, reference is repeatedly made to liquids containing a blood sample analysis and histograms obtained from such liquids for blood cell analysis, it will be understood that this reference is made merely for the purpose of providing the following explanations with respect to actually investigated examples. In fact, the inventive method and apparatus can be readily utilized for carrying out a particle analysis on many other particle containing fluids possessing particle population maxima and minima at certain measured values of the predetermined particle parameter.

The inventive apparatus 100 as illustrated in FIG. 1 of the drawings, receives and stores the pulses or signals which are indicative of the measured value of the predetermined parameter of the particles and also the count of the number of particles of the sample which is passed through the detection zone of the measuring device 20. Subsequently, the received and stored measured values and counts are arranged in the form of individual histograms of the type as illustrated in FIGS. 2 through 5. Each such individual histogram is evaluated in terms of particle distribution as a function of the predetermined particle parameter, for example, the blood cell distribution as a function of the blood cell size or volume. Each such individual histogram contains a number of particle population maxima which are separated by particle population minima. By utilizing appropriately selected separation threshold values, the integral under the particle population maxima can be determined in order to thereby determine the concentrations of the different types of particles in the investigated sample of the particle containing fluid.

The inventive apparatus 100 thus constitutes evaluating means which are connected with the measuring device 20 and which contain as primary components first storage means 50, second storage means 85 and third storage means 95 as well as a first computing section 60, a second computing section 70, a third computing section 80 and a fourth computing section 90. In order to facilitate the following explanations with respect to the structure and function of the various components of the inventive apparatus 100, the different components will be discussed with reference to respectively associated operation steps which are designated by reference characters 1 through 15 placed into the respective blocks. Specifically, the first storage means 50 and the first computing section 60 as well as the second computing section 70 perform method steps designated by the reference characters 1 through 7. Such method steps 1 through 7 constitute conventional method steps which are used in the prior art methods and apparatuses performing a particle analysis.

The method steps and the associated components will now be described as follows:

The first storage means 50 are interconnected between the measuring device 20 and the first computing section 60. The first storage means 50 and the first computing section 60 constitute arranging means 50, 60 for arranging the measured values of the predetermined particle parameter of the particles and the number of particles which are associated with such measured values in the form of an individual histogram of the general type, for instance, as shown in FIG. 2.

Figure 2:
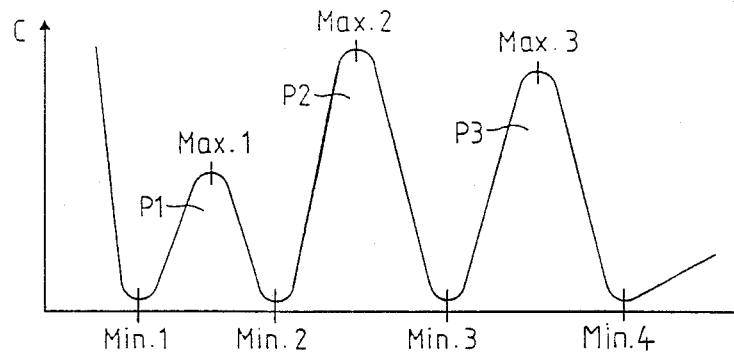
FIG. 2 shows a typical histogram of a general type which can be processed and evaluated in the apparatus shown in FIG. 1.

Each such individual histogram, as illustrated, contains a predetermined number of particle population maxima, for example, the population particle maxima Max.1, Max.2 and Max.3 as illustrated in FIG. 2 of the drawings. Each one of the particle population maxima Max.1, Max.2 and Max.3 is bounded by sufficiently distinct and resolved particle population minima, namely the particle population maximum Max.1 is bounded by the particle population minima Min.1 and Min.2, the particle population maximum Max.2 is bounded by the particle population minima Min.2 and Min.3, and the particle population maximum Max.3 is bounded by the particle population minima Min.3 and Min.4. In order to arrange the received measured values and particle numbers, the first storage means 50 contain a predetermined number of storage channels which store the measured values under associated storage channel addresses.

The first storage means 50 perform a data organization step 1 and a data storing step 2.

During the data organization step 1, there is first estimated the range of the measured values of the predetermined particle parameter which covers the expected particle distribution. There are then defined discrete steps of a predetermined magnitude within the estimated range of the expected particle distribution. The number of storage channels in the first storage means 50 is then defined in accordance with defined discrete step magnitudes and the estimated range of the expected particle distribution. Absolute measured values of the predetermined particle parameter are discriminated with respect to the predetermined particle parameter, for example, in an increasing sequence and associated with respective storage channels in the first storage means 50. During this data organization step 1, there are also defined the decision criteria for a particle analysis, such as, for example, the criteria defining relative or insufficiently resolved particle population minima, incrementing steps and so forth.

During the data storing step 2 in the first storage means 50, the measured values are detected in real time by means of the electrically and/or optically operating detection means of the measuring device 20. The measured values received from such detection means are digitized and the digitized measured values are associated with the correspondingly indexed storage channels of the first storage means 50. A plurality of storage channel addresses is determined and each such storage channel address is associated with the digitized measured values.

As already explained hereinbefore, the first computing section 60 constitutes a further component of the arranging means 50, 60 for arranging the measured values in the form of a histogram of the type as illustrated in FIGS. 2 through 5. The first computing section 60 is connected to the first storage means 50 and performs a preprocessing step 3, a selection step 4, a minimum search 5 and a checking and decision-making step 6. In detail, such steps encompass the following operations:

During the preprocessing step 3, quantization errors are reduced and such quantization errors are due to the digitizing operation upon the incoming measured values. Furthermore, there is applied a first or, if required, a higher order compensating or smoothing operation to the digitized data having reduced quantization errors.

During the selecting step 4, there are fixed the limits of a number N of coherent storage channel addresses required for detecting a particle population minimum such as, for example, the particle population minimum Min.1, Min.2 or Min.3. Furthermore, during the selection step 4, there may also be fixed in an analogous manner the limits for detecting a population particle maximum such as, for example, the particle population maxima Max.1, Max.2 or Max.3 in FIG. 2.

During the minimum searching step 5, respective algorithms are utilized for determining the particle population minimum by mutually comparing the digitized measured values stored under the number N of storage channel addresses which have been determined during the selecting step 4.

During the checking and decision-making step 6, there is checked whether the thus determined particle population minimum constitutes a relative minimum or an absolute minimum. The decision criteria which have been defined during the data organizing step 1, are utilized when there occur relative particle population minima. If desired, corresponding decision criteria are utilized in analogous manner for checking the determined particle population maxima. If no particle population minima are detected, the related individual histogram is analyzed for its analytical relevance, for example, by checking the haematologic significance of the histogram or by checking for the presence of apparatus deficiencies.

The second computing section 70 is associated with the first computing section 60 and performs a minimum utilizing step 7. During this step of the operation, the integrals are formed on both sides of the determined particle population minimum such as, for example, the particle population minimum Min.2 or Min.3 in the histogram illustrated in FIG. 2. The particle population minimum which has been determined during the minimum searching step 5, is associated with the separation threshold value separating two adjacent particle populations. The integration over the particle population maximum between the integration limits determined by the associated particle population minima or separation threshold or separation threshold values ultimately has as its result a determination of the concentration of the related particles in the sample of the particle containing fluid which has been investigated by the measuring device 20.

During this minimum utilizing step 7, there is also outputted the result of the particle analysis of the sample which has been investigated by the measuring device 20.

The second computing section 70 further contains control signal generating means 71 which generate a control signal for initiating measurement of a further sample of the particle containing fluid; further control signals are outputted for controlling the operation of further apparatus components which are connected to the measuring device 20, for example, a diluter in an automatic sample processor. Also, during the minimum utilizing step 7, the second computing section 70 gives required instructions to a user of the apparatus 100.

The method steps and structural components which have been described hereinbefore and which are required, for example, for a blood cell analysis in a sample of a liquid containing a blood sample, are essentially known from the initially mentioned European Patent Publication No. 0,012,418 and the cognate U.S. Pat. No. 4,309,757. This known apparatus also ensures in the presence of suitable particle distributions, for instance, with respect to size, an automatic or adaptive location of separation thresholds or separation threshold values for discriminating between overlapping particle populations, i.e. overlapping particle population maxima and related particle population minima.

Figure 3:
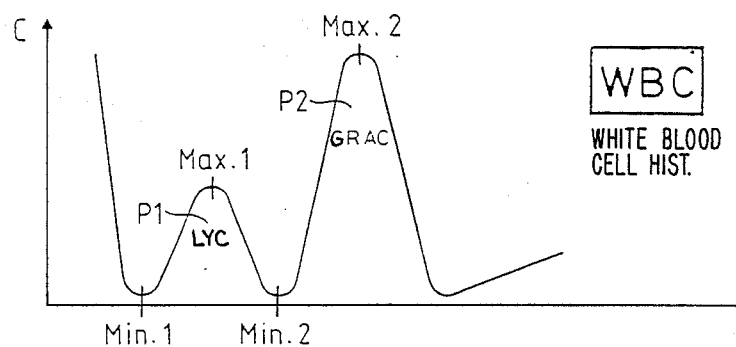
FIG. 3 shows a typical histogram obtained by a blood cell analysis and which histogram shows sufficiently distinct or resolved particle population minima and can be processed and evaluated in the apparatus shown in FIG. 1.

For instance, in blood cell analysis such apparatus is suitable for analyzing histograms of the type as illustrated in FIG. 3. Such histogram is basically composed of a first particle population maximum Max.1 which is bounded by two sufficiently resolved particle population minima Min.1 and Min.2 and which corresponds to a first particle population P1 formed by lymphocytes LYC. A second particle population maximum Max.2 follows the particle population minimum Min.2 and indicates a particle population P2 of granulocytes GRAC. Since the two particle populations P1 and P2 overlap only to a relatively small extent and the particle population minimum Min.2 is sufficiently distinct or resolved, the areas under the two particle population maxima Max.1 and Max.2 and thereby the particle populations P1 and P2 can be determined by integration in the aforementioned apparatus without any great difficulty.

Figure 4:
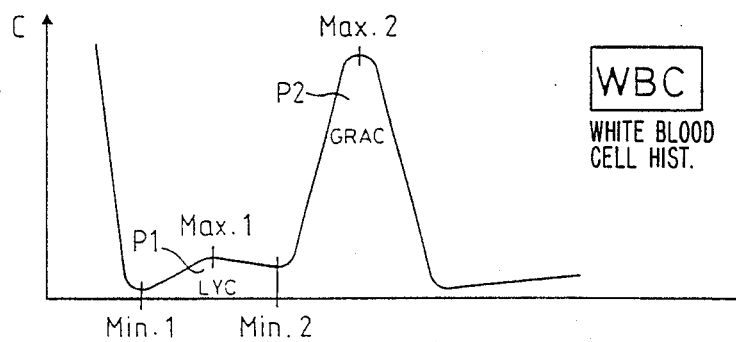
FIG. 4 shows a histogram obtained by a blood cell analysis and which histogram contains an insufficiently resolved particle population minimum but can be processed and evaluated in the apparatus shown in FIG. 1.

In the event of a blood sample containing a relatively small lymphocyte concentration, there is observed a considerable overlap between the two particle populations P1 and P2 as illustrated in the histogram shown in FIG. 4. As a result of the greater overlap between the particle populations P1 and P2, the particle population minimum Min.2 is insufficiently distinct or resolved between the particle population maxima Max.1 and Max.2. In fact, the particle population minimum Min.2 is insufficiently distinct or resolved for determining the lymphocyte population P1 by means of the separation thresholds or separation threshold values utilized in the apparatus according to the aforementioned European Patent Publication No. 0,012,418. Since, as a result, the separation threshold or separation threshold value, which is associated with the insufficiently distinct or resolved particle population minimum Min.2, is insufficiently defined, no precise and useful result can be obtained when such apparatus is utilized for the particle analysis of a particle containing fluid resulting in a histogram of the type as illustrated in FIGS. 4 and 5.

Figure 5:
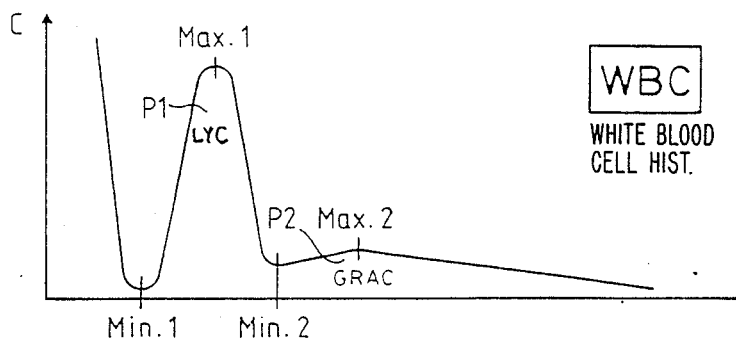
FIG. 5 shows a further histogram obtained by a blood cell analysis and which histogram contains an insufficiently resolved particle population minimum but can be processed and evaluated in the apparatus shown in FIG. 1.

The inventive method and apparatus permits processing and successfully evaluating histograms containing insufficiently distinct or resolved particle population minima like the particle population minima Min.2 shown in FIGS. 4 and 5. The primary components of the inventive apparatus 100 for achieving this beneficial result are constituted by second storage means 85 and third storage means 95 as well as a third computing section 80 and a fourth computing section 90. In the same manner as described hereinbefore, different blocks of these components are designated by respective reference characters which indicate the method steps which are performed by the related structural components. The components, their interconnection and the method steps performed by the components are now described herein as follows:

The third computing section 80 interconnects the first computing section 60 and the second computing section 70 and constitutes means for determining at least one selected characteristic predetermined difference quotient Q associated with at least one sufficiently resolved particle population minimum in a predetermined number of selected histograms. In effect, the third computing section performs a difference quotient determining step 8 during which difference quotients Q of the type as explained further hereinbelow are determined for each individual histogram. There is thus obtained a series of all possible difference quotients Q.

The second storage means 85 are interconnected between the second computing section 70 and the third computing section 80 and performs a storing step 9. During this storing step 9, the difference quotients Q which have been determined during the difference quotient determining step 8 in the third computing section 80, are ordered and stored in the second storage means 85. Furthermore, the second storage means 85 form a mean value of all those or selected difference quotients Q which are stored in the second storage means 85 and which are related to predetermined insufficiently defined separation thresholds or separation threshold values associated with insufficiently distinct or resolved particle population minima.

During a selecting step 10, the third computing section fixes criteria in relation to an insufficiently defined separation threshold value which is associated with an insufficiently resolved particle population minimum in a histogram, for example, of the type as illustrated in FIGS. 4 and 5. Such insufficiently distinct or resolved particle population minimum has already been determined during the checking and decision-making step 6 performed by the first computing section 60. During the selecting step 10, the third computing section 80 further selects a selected difference quotient Q which has been determined during the difference quotient determining step 8 and stored in the second storage means 85 and which corresponds to the insufficiently defined separation threshold or separation threshold value to be fixed or determined and associated with the insufficiently distinct or resolved particle population minimum.

The third computing section 80 further performs a checking and decision-making step 11 in cooperation with the second storage means 85 and the third storage means 95 which are also connected to the third computing section 80. During this checking and decision-making step 11, the third computing section 80 determines whether a selected difference quotient Q is present for the insufficiently defined separation threshold or separation threshold value to be determined and the criteria for fixing the same have been fixed during the selecting step 10 in the third computing section 80. In the absence of such selected difference quotient Q, the histogram containing the insufficiently defined separation threshold or separation threshold value is outputted from the third computing section 80 and stored in the third storage means 95.

In the presence of such selective difference quotient Q, the next steps of the inventive method are performed in the fourth computing section 90.

The fourth computing section 90 interconnects the second computing section 70 and the third computing section 80 and constitutes means for determining, on the basis of the selected difference quotient Q, the separation threshold value associated with the insufficiently distinct or resolved particle population minimum such as, for example, the particle population minimum Min.2 in the histograms shown in FIGS. 4 and 5. For this purpose, the fourth computing section 90 performs a threshold determining step 12. During this step the insufficiently defined separation threshold or separation threshold value which is associated with the insufficiently distinct or resolved particle population minimum, is determined on the basis of the selected difference quotient Q stored in the second storage means 85 and in a manner more fully explained hereinafter.

The fourth computing section 90 further contains boundary condition fixing means 91. Such boundary condition fixing means 91 fix the boundary conditions for the insufficiently defined separation threshold or separation threshold value which has been determined during the separation threshold determining step 12 on the basis of the selected characteristic predetermined difference quotient Q. The boundary conditions require that the separation threshold value which is determined on the basis of the selected characteristic predetermined difference quotient Q, occurs within a preset range of the predetermined parameter value such as, for example, the size or volume of the investigated particles, for example, blood cells.

If the thus determined separation threshold or separation threshold value appears within the fixed boundary conditions, i.e. within the preset range of the predetermined particle parameter, the thus determined separation threshold or separation threshold value is supplied to the second computing section 70 in order to perform the evaluation of the histogram during the minimum utilizing step 7.

If the thus determined separation threshold or separation threshold value appears outside of the fixed boundary conditions or outside the preset range of the predetermined particle parameter, the fourth computing section 90 generates a corresponding signal at an output unit 72 of the second computing section 70. The output unit 72 gives corresponding instructions to the operator of the apparatus 100 or another appropriately designed component of the inventive apparatus 100.

The histograms containing an insufficiently defined separation threshold or separation threshold value associated with an insufficiently distinct or resolved particle population minimum and for which histogram no selected characteristic predetermined difference quotient Q could be found during the checking and decision-making step 11 carried out by the third computing section 80, are stored in the third storage means 95. Such histograms, however, are only intermittently stored in the third storage means 95 and the stored histogram is repeatedly circulated through the selecting step 10 and the checking and decision-making step 11 until a related characteristic predetermined difference quotient Q is found and the histogram can be analyzed by the separation threshold determining step 12 and the checking and decision-making step 13 in the fourth computing section 90. This intermittent storing step is designated by the reference numeral 14 in connection with the third storage means 95.

If no related characteristic predetermined difference quotient Q can be found after repeated circulation of the histogram stored in the third storage means 95, a corresponding signal is issued by the fourth computing section 90 to the output unit 72 of the second computing section 70. During a non-analyzable histogram detection step 15, therefore, the output unit 72 signals the presence of (i) a histogram containing an insufficiently defined separation threshold or separation threshold value and the absence of a related characteristic predetermined difference quotient Q and (ii) a separation threshold value which is determined on the basis of a related characteristic predetermined difference quotient Q but is located outside the fixed boundary conditions.

In the following, FIGS. 2 through 5 of the drawings and specifically the characteristic predetermined difference quotient Q will be once again discussed in more detail. FIGS. 2 through 5 show schematically illustrated histograms containing differently distinct or resolved particle populations or particle distributions. In each such histogram or particle population or particle distribution curve, the values on the ordinate are representative of the counting frequency or number of counts C of the particles which are contained in the investigated sample of the particle containing fluid. The values on the abscissa represent the peak values of the measured pulse or signal voltage during the scanning operation performed upon the particles of the particle containing fluid which is passed through the detection zone of the measuring device 20. This peak value of the measured pulse or signal voltage corresponds to a predetermined particle parameter like, for example, the size or volume of the particles.

FIG. 2 shows a histogram of a general type which can be obtained during a particle analysis. Such histogram contains, for example, the particle populations P1, P2 and P3 and there are indicated in the particle population or particle distribution curve, the particle population maxima Max.1, Max.2 and Max.3 as well as the particle population minima Min.1, Min.2 and Min.3.

FIG. 3 shows a WBC or white blood cell histogram obtained during the particle analysis of white blood cells contained in a blood sample which, for example, may be dispersed in a liquid which is passed through the detection zone of the measuring device 20. There can be identified two particle populations P1 and P2, and in the particle population or particle distribution curve, the particle population maxima Max.1 and Max.2 as well as the particle population minima Min.1 and Min.2.

The two particle or cell populations P1 and P2 illustrated by the white blood cell histogram in FIG. 3 comprise granulocytes GRAC and lymphocytes LYC which are present in mutually different and sufficiently distinct or resolved ranges of the predetermined particle or cell parameter. As a result, the concentrations of the granulocytes GRAC and the lymphocytes LYC can be readily determined by setting related separation thresholds or separation threshold values in accordance with the known method which has been described hereinbefore by the method steps 1 through 7, as already noted hereinbefore.

In FIG. 4 there is illustrated as a selected example a WBC or white blood cell histogram for the particle or blood cell analysis and such histogram shows only one distinct or pronounced particle or cell population P2 of granulocytes GRAC defining a particle or cell population maximum Max.2. The less pronounced cell or particle population P1 of lymphocytes LYC defines a particle or cell population maximum Max.1 with respect to two particle or cell population minima Min.1 and Min.2. In fact, as already noted hereinbefore, the particle or cell population minimum Min.2 is insufficiently distinct or resolved in comparison to the corresponding particle or cell population minimum Min.2 in the sufficiently or fully resolved histogram shown in FIG. 3. Moreover, the separation threshold or separation threshold value associated with the insufficiently distint or resolved particle cell or population minimum Min.2, is insufficiently defined and thus cannot be properly determined using the known particle analysis method as described hereinbefore with reference to the method steps 1 through 7. The insufficient resolution of the two particle or cell populations in the histogram illustrated in FIG. 4 is a consequence of the relatively small concentration of lymphocytes LYC as compared to the histogram shown in FIG. 3.

FIG. 5 shows a further selected WBC or white blood cell histogram for the particle or blood cell analysis which has been obtained from a blood sample containing a relatively small concentration of granulocytes GRAC. In the histogram illustrated in FIG. 5, therefore, the particle or cell population P1 is distinctly pronounced and defines a particle or cell population maximum Max.1 and a sufficiently distinct or resolved particle or cell population minimum Min.1. The particle or cell population P2 of granulocytes GRAC is small and less distinctly pronounced with a particle or cell population maximum Max.2 and an associated particle or cell population minimum Min.2. The particle or cell population minimum Min.2 between the two particle or cell populations P1 and P2 is insufficiently distinct or resolved and, therefore, the separation threshold or separation threshold value separating the two particle or cell populations P1 or P2 is insufficiently defined and the particle or cell analysis fails on the basis of the known method as described hereinbefore with reference to method steps 1 through 7.

It should be noted that histograms of the general type as illustrated in FIGS. 4 and 5, although described merely by way of example and not limitation with reference to the determination of the concentration of lymphocytes LYC and granulocytes GRAC in a blood sample, also can be obtained during the particle analysis of many other particle containing fluids particularly in the event of relatively widely differing particle concentrations.

In such histograms the different particle or cell populations P1 and P2 cannot be positively differentiated when utilizing the known method of analysis as described hereinbefore with reference to method steps 1 through 7. As already explained hereinbefore, the reason therefore is that the separation thresholds or separation threshold values are insufficiently defined due to the fact that the associated particle or cell population minima such as the illustrated particle or cell population minimum Min.2 are insufficiently distinct or resolved. The inventive method and apparatus provide the means for sufficiently precisely determining, during the particle or cell analysis, from such insufficiently distinct or resolved histograms the separation thresholds or separation threshold values on the basis of a characteristic predetermined difference quotient associated with the insufficiently distinct or resolved particle or cell population minimum like the particle or cell population minimum Min.2 in FIGS. 4 and 5.

The inventive method can be utilized in the presence of histograms of the type as illustrated in FIGS. 3, 4 and 5 with respect to the determination of the concentration of lymphocytes LYC and granulocytes GRAC from a blood sample but, of course, as already noted before can be utilized with respect to corresponding histograms which are obtained from other samples of particle containing fluids. The inventive method is based on the determination of at least one characteristic predetermined difference quotient Q which is related to at least one insufficiently distinct or resolved particle or cell population minimum such as, for instance, the particle or cell population minimum Min.2 in the histograms of FIGS. 4 and 5. This characteristic predetermined difference quotient Q is determined during the difference quotient determining step 8 of the inventive method and is carried out with reference to a histogram which contains the corresponding particle or cell population minimum Min.2 in a sufficiently distinct or resolved condition such as the histogram illustrated in FIG. 3. The determination of the characteristic predetermined difference quotient which is associated with the particle or cell population minimum Min.2, is carried out on the basis of Equation (1) as given hereinbelow:

$$Q_2(1,2)_{res} = \frac{Min.(2) - Min.(1)}{Max.(2) - Min.(1)} \quad (1)$$

Therein $Q_2(1,2)$ constitutes the required or selected characteristic predetermined difference quotient, Min.(2) is the measured value of the predetermined particle parameter, namely the cell size or volume at the location of the particle or cell population minimum Min.2, Min.(1) is the measured value of the predetermined particle parameter, namely the cell size or volume at the location of the particle or cell population minimum Min.1, and Max.(2) is the measured value of the predetermined particle parameter, namely the cell size or volume at the location of the particle or cell population maximum Max.2.

This characteristic predetermined difference quotient $Q_2(1,2)_{res}$ is utilized for determining the separation threshold or separation threshold value $S_2(1,2)_{unres}$ which constitutes an originally insufficiently defined separation threshold or separation threshold value. This is due to the fact that the original separation threshold or separation threshold value $S_2(1,2)_{unres}$ is associated with an insufficiently distinct or resolved particle or cell population minimum such as the particle or cell population minimum Min.2 in the histograms of the type as illustrated in FIGS. 4 and 5. However, such originally insufficiently defined separation threshold or separation threshold value $S_2(1,2)_{unres}$ can be sufficiently distinctly determined on the basis of the characteristic predetermined difference quotient $Q_2(1,2)_{res}$ which was determined on the basis of the histogram illustrated in FIG. 3 and which histogram contains a sufficiently distinct or resolved particle or cell population minimum Min.2 and which corresponds to the insufficiently distinct or resolved particle or cell population minimum Min.2 in the histograms illustrated in FIGS. 4 and 5. The originally insufficiently defined separation threshold or separation threshold value $S_2(1,2)_{unres}$ is determined on the basis of the characteristic predetermined difference quotient $Q_2(1,2)_{res}$ in accordance with Equation (2):

$S_2(1,2)_{unres} =$
$(Max.(2) - Min.(1))_{unres} \cdot Q_2(1,2)_{res} + Min.(1)_{unres}$ (2)

Therein $S_2(1,2)_{unres}$ constitutes the desired, originally insufficiently defined separation threshold or separation threshold value, Max.(2) is the measured value of the predetermined particle parameter, namely the cell size or volume at the location of the particle or cell population maximum Max.2 in the insufficiently resolved histogram, Min.(1) is the measured value of the predetermined particle parameter, namely the cell size or volume at the location of the particle or cell population minimum Min.1, in the insufficiently resolved histogram and $Q_2(1,2)_{res}$ is the characteristic predetermined difference quotient associated with the corresponding particle population minimum Min.2 in the sufficiently resolved histogram.

Thus, in its specific utilization with respect to the blood cell analysis in blood samples, the inventive method and apparatus 100 is generally designed with the view of determining an originally insufficiently defined separation threshold or separation threshold value $(S_x)_{unres}$ which is associated with a predetermined insufficiently distinct or resolved particle or cell population minimum such as, for example, the particle or cell population minimum Min.2 as illustrated in FIGS. 4 and 5 with respect to histograms resulting from a WBC or white blood cell analysis. When a plurality of blood samples is subjected to such WBC or white blood cell analysis, such plurality of blood samples is composed of blood samples resulting in sufficiently or fully resolved histograms like the histogram illustrated in FIG. 3. Additionally, such plurality contains blood samples resulting in histograms which display insufficiently distinct or resolved particle or cell population minima like the particle of cell population minimum Min.2 illustrated in FIGS. 4 and 5. The inventive method and apparatus 100 now permits successfully analyzing the blood samples which result in histograms of the type as illustrated in FIGS. 4 and 5. Such blood cell analysis can be even more refined by relying on mean values of the selected characteristic predetermined difference quotient $Q_x$ and such mean values are formed and stored in the second storage means 85 during the difference quotient storing step 9 of the inventive method. There is thus obtained, as a result of the analysis of a plurality of WBC or white blood cell histograms in accordance with the aforedescribed method a value of 0.59±0.04 for the characteristic predetermined difference quotient $Q_2(1,2)_{res}$ as determined by the Equation (1) given hereinbefore.

As already indicated hereinbefore, the inventive method and apparatus 100 can be utilized in a corresponding manner for carrying out a particle analysis of other particle containing fluids which result in differently structured histograms and may also be applied in the presence of more than one insufficiently distinct or resolved particle population minimum. In such more generalized case, each characteristic predetermined difference quotient $Q_x(j,k)$ is determined in a first step in accordance with the general Equation (1') as given hereinbelow:

$$Q_x(j,k)_{res} = \frac{Min.(x) - Min.(j)}{Max.(k) - Min.(j)} \quad (1')$$

Therein $Q_x(j,k)_{res}$ constitutes an x-th selected characteristic predetermined difference quotient determined from a histogram containing the sufficiently resolved particle population maximum Max.k and sufficiently or fully resolved particle population minima Min.x and Min.j;

x is an index relating the characteristic predetermined difference quotient $Q_x(j,k)_{res}$ to the particle population minimum Min.x and the associated separation threshold or separation threshold value to be located or determined;

Min.(x) is the measured value of the predetermined particle parameter at the location of a first sufficiently distinct or resolved particle population minimum Min.x related to an insufficiently distinct or resolved particle population minimum associated with an insufficiently defined separation threshold or separation threshold value in a less distinctly resolved histogram;

Min.(j) is the measured value of the predetermined particle parameter at the location of a second sufficiently distinct or resolved particle population minimum Min.j;

j is an index relating to the second and sufficiently distinct or resolved particle population minimum Min.j which is not associated with an originally insufficiently defined separation threshold or separation threshold value and which particularly can be determined by means of an automatic or adaptive finding operation;

Max.(k) is the measured value of the predetermined particle parameter at the location of a particle population maximum Max.k which is sufficiently distinct or resolved and can be readily determined; and k is an index relating to such sufficiently pronounced and readily determinable particle population maximum Max.k.

On the basis of this generalized characteristic predetermined difference quotient $Q_x(j,k)_{res}$ the originally insufficiently defined separation threshold or separation threshold value $S_x(j,k)_{unres}$ is determined in accordance with the following Equation (2'):

$$S_x(j,k)_{unres} = (Max.(k) - Min.(j))_{unres} \cdot Q_x(j,k)_{res} + Min.(j)_{unres} \quad (2')$$

Therein $S_x(j,k)_{unres}$ constitutes the x-th separation threshold or separation threshold value which is associated with the insufficiently distinct or resolved particle population minimum Min.x and which is determined on the basis of the particle population maximum Max.k and the particle population minima Min.j and the characteristic predetermined difference quotient $Q_x(j,k)_{res}$.

The other members of Equation (2') have the same meaning as the corresponding members in Equation (1').

When carrying out the particle analysis on a plurality of samples of a particle containing fluid, thus, an individual histogram is produced for each individual sample. In each such histogram the separation thresholds or separation threshold values are defined by related criteria in order to determine the related particle populations. Furthermore, and likewise there are compiled all possible characteristic predetermined difference quotients $Q_x(j,k)_{res}$ for for each individual histogram. When a sample produces a histogram containing at least one insufficiently distinct or resolved particle population minimum Min.x with which there is associated at least one insufficiently defined separation threshold or separation threshold value $S_x(j,k)_{unres}$, such at least one originally insufficiently defined separation threshold or separation threshold value $S_x(j,k)_{unres}$ is determined on the basis of at least one selected characteristic predetermined difference quotient $Q_x(j,k)_{res}$ which has already been compiled.

If no such selected characteristic predetermined difference quotient $Q_x(j,k)_{res}$ which is related to the insufficiently distinct or resolved particle population minimum Min.x, is available at the time of the analysis of the histogram containing the insufficiently distinct or resolved particle population minimum, such histogram is intermittently stored in the third storage means 95. This histogram is circulated through the third computing section 80 of the inventive apparatus 100 until the selected characteristic predetermined difference quotient $Q_x(j,k)_{res}$ has been determined and can be utilized for determining the originally insufficiently defined separation threshold or separation threshold value $S_x(j,k)_{unres}$.

Due to the aforementioned formation of mean values of the selected characteristic predetermined difference quotients $Q_x(j,k)_{res}$ in the second storage means 85, the precision in the determination of the selected characteristic predetermined difference quotients $Q_x(j,k)_{res}$ and the separation thresholds or separation threshold values $S_x(j,k)_{unres}$ determined on the basis of such characteristic predetermined difference quotients $Q_x(j,k)_{res}$ increases with an increasing number of determinations of the extreme values, i.e. the particle population maxima and particle population minima, and thus with an increasing number of analyzed samples of the particle containing fluid.

When carrying out the inventive method of particle analysis with respect to a multitude of blood samples and related WBC or white blood cell histograms, it has been found that the characteristic predetermined difference quotients Q which have been determined on the basis of Equations (1) or (1') and which were associated with the same class or type of insufficiently distinct or resolved particle population minima, had a substantially constant value which was afflicted with only small and practically negligible deviations. As a result of such experiments it was found that the mean value of the characteristic predetermined difference quotient $Q_2$ or $Q_x$, as the case may be, which is determined in the manner as described hereinbefore with respect to the steps 8 and 9 of the inventive method, is sufficiently invariant in good approximation. Consequently, the determination of the originally insufficiently defined separation thresholds or separation threshold values $S_2$ or $S_x$, as the case may be, in accordance with Equations (2) or (2') is preferably determined on the basis of the mean values of the characteristic predetermined difference quotient $Q_2$ or $Q_x$, as the case may be.

The aforementioned mean values of the characteristic predetermined difference quotients $Q_x(j,k)_{res}$ are preferably filed or stored in suitable storage means for further use for the same type of particle analysis, for example, WBC or white blood cell measurements. The mean values of the selected characteristic predetermined difference quotients $Q_x(j,k)_{res}$, for example, can be stored in the second storage means 85 and can be made available, if required. For this purpose there are provided in the third computing section 80 verifying and adapting means 81 for verifying the mean value of the selected characteristic predetermined difference quotient $Q_x(j,k)_{res}$ in relation to an associated sufficiently resolved particle population minimum Min.x and adaptively optimizing the selected characteristic predetermined difference quotient $Q_x(j,k)_{res}$ with respect to such associated sufficiently resolved particle population minimum Min.x. Binding or standard values for originally insufficiently defined separation thresholds or separation threshold values $S_x(j,k)_{unres}$ can thus be provided on the basis of such verified and adaptively optimized mean values of the related characteristic predetermined difference quotients $Q_x(j,k)_{res}$.

According to experience, the inventive method should only be applied if the histogram which is subjected to the analysis, satisfies certain conditions. These conditions are set in the first computing section 60 and during the checking and decision-making step 6 of the inventive method the histogram containing at least one insufficiently distinct or resolved particle population minimum Min.x is investigated with respect to certain boundary conditions. If, for example, during a WBC or white blood cell analysis in accordance with the known method as described in the initially mentioned European Patent Publication 0,012,418, the particle population minimum designated Min.2 in FIG. 4 cannot be determined, then, the inventive method is used complementary to the known method. This is predicated upon the condition that the aforementioned boundary conditions are 40 fl < Min.1 < 120 fl and 140 fl < Max.2 < 220 fl. If these boundary conditions are not met by a histogram to be evaluated, such histogram is not further analyzed for lymphocytes LYC. These volumina 40 fl to 220 fl are within the range of values usually obtained in histograms for WBC or white blood cell analysis. If insufficiently defined separation thresholds or separation threshold values are intended to be determined for particle populations or distributions other than WBC or white blood cells, of course, different boundary conditions are valid or set.

Experience has further shown that the separation thresholds or separation threshold values $S_x(j,k)_{unres}$ which are associated with insufficiently distinct or resolved particle population minima Min.x and which are determined on the basis of the related characteristic predetermined difference quotient $Q_x(j,k)_{res}$, must satisfy predetermined, i.e. fixed or set boundary conditions. For this purpose, the fourth computing section 90 contains means 91 for fixing or setting such boundary conditions and for determining whether the separation threshold or separation threshold value $S_x(j,k)_{unres}$ which has been determined on the basis of the characteristic predetermined difference quotient $Q_x(j,k)_{res}$, satisfies such fixed or set boundary conditions. In the event that the thus determined separation threshold or separation threshold value $S_x(j,k)_{unres}$ is located outside the fixed or set boundary conditions, the associated histogram is not subjected to further analysis as already described hereinbefore with respect to the checking and decision-making step 13 of the inventive method.

Although the inventive method and apparatus 100 provide significantly extended possibilities for determining originally insufficiently defined separation thresholds or separation threshold values $S_x(j,k)_{unres}$, it may still occur that individual histograms cannot be automatically evaluated. The reasons therefore may be that there is not available a statistically sufficiently significant value for the selected characteristic predetermined difference quotient $Q_x(j,k)_{res}$, the histogram does not satisfy the required boundary conditions, for example, if the related extreme particle population values such as the particle population minimum Min.j and the particle population maximum Max.k are afflicted with errors or not located within an expected interval. In those cases the related histograms are also stored, for example, in the third storage means 95 and held available for further examination or evaluation in accordance with other methods of analysis. For this purpose, the output unit 72 provided in the second computing section 70 gives a corresponding instruction either to the operator or a further unit or component which is associated with the inventive apparatus 100.

The inventive method as well as the inventive apparatus 100 for carrying out the inventive method are independently operable, however, the essential components required for determining the separation thresholds or separation threshold values $S_x(j,k)_{unres}$ which are associated with insufficiently distinct or resolved particle population minima Min.x like, for example, the particle or cell population minimum Min.2 in the histograms illustrated in FIGS. 4 and 5, on the basis of the characteristic predetermined difference quotients $Q_x(j,k)_{res}$ and the associated method steps are complementary to the known method and apparatus as described in the initially mentioned European Patent Publication No. 0,012,418. The inventive method steps and apparatus components thus can also be integrated with the known method and the known apparatus for particle analysis. In either way, the inventive method and apparatus permits determining substantially all of the characteristic magnitudes for a particle population or distribution even in the presence of insufficiently distinct or resolved particle population minima Min.x. The selected characteristic predetermined difference quotients $Q_x(j,k)_{res}$ and the separation thresholds or separation threshold values $S_x(j,k)_{unres}$ which are related to the insufficiently distinct or resolved particle population minima Min.x, thus can be determined as well as checked, verified and adaptively optimized and permit compiling corresponding data banks for particle analysis of further particle containing fluids.

It is further noted that the separation threshold or separation threshold value $S_x(j,k)_{unres}$ which is determined on the basis of the related characteristic predetermined difference quotient $Q_x(j,k)_{res}$, constitutes an electrical signal which is present and processed within the inventive apparatus 100 and is supplied to a suitable unit or component which is operatively connected with the inventive apparatus 100 for controlling associated output units such as, for example, a printer and/or a display.

While there are shown and described present preferred embodiments of the invention, it is to be distinctly understood that the invention is not limited thereto, but may be otherwise variously embodied and practiced within the scope of the following claims. Accordingly,

What I claim is:

1. A method of analyzing particles dispersed in a fluid, comprising the steps of:
    measuring values of a predetermined particle parameter and the number of particles associated with said measured values and contained in individual samples of a predetermined number of samples of the particle containing fluid;
    arranging said measured values of said predetermined particle parameter and said number of said particles in said individual samples in the form of individual histograms of a predetermined number of histograms related to said predetermined number of samples of said particle containing fluid, each of said individual histograms containing a predetermined number of particle population maxima and a predetermined number of particle population minima;
    determining from said individual histograms, separation threshold values associated with sufficiently resolved ones of said predetermined number of particle population minima;
    detecting in said predetermined number of histograms, selected histograms containing at least one insufficiently resolved particle population minimum unsuitable for directly determining at least one related separation threshold value;
    determining in said predetermined number of histograms, at least one selected characteristic predetermined difference quotient associated with at least one sufficiently resolved particle population minimum which corresponds to said at least one insufficiently resolved particle population minimum in said selected histograms;
    determining in said selected histograms at least one separation threshold value associated with said at least one insufficiently resolved particle population minimum on the basis of said at least one selected characteristic predetermined difference quotient; and
    utilizing said separation threshold values and said at least one separation threshold value determined on the basis of said selected characteristic predetermined difference quotient for determining the particle distribution as a function of said predetermined particle parameter in each individual sample of said predetermined number of samples of said particle containing fluid.

2. The method as defined in claim 1, further including the steps of:
    determining a predetermined number of characteristic predetermined difference quotients for each one of a predetermined number of said individual histograms;
    storing said predetermined number of characteristic predetermined difference quotients; and
    selecting from said stored characteristic predetermined difference quotients, said at least one selected characteristic predetermined difference quotient.

3. The method as defined in claim 2, further including the steps of:
    forming and storing at least one mean value of said at least one selected characteristic predetermined difference quotient; and
    said step of determining in said selected histograms, said at least one separation threshold value associated with said at least one insufficiently resolved particle population minimum, entailing the step of determining said at least one separation threshold value in said selected histograms on the basis of said mean value of said at least one selected characteristic predetermined difference quotient.

4. The method as defined in claim 2, further including the steps of:
    storing said selected histogram in the absence of of said at least one selected stored characteristic predetermined difference quotient associated with said at least one insufficiently resolved particle population minimum in said selected histograms; and
    postponing said step of determining said at least one separation threshold value in said selected histograms until said at least one selected characteristic predetermined difference quotient has been determined.

5. The method as defined in claim 1, further including the steps of:
    fixing boundary conditions for said at least one separation threshold value associated with said at least one insufficiently resolved particle population minimum; and
    after said step of determining, in said selected histograms, said at least one separation threshold value associated with said at least one insufficiently resolved particle population minimum, determining whether the at least one separation threshold value satisfies said fixed boundary conditions.

6. The method as defined in claim 1, further including the steps of:
    feeding said measured values of said predetermined particle parameter and said number of particles associated with said measured values to a first computing section of a predetermined number of computing sections; and preprogramming said predetermined number of computing sections for processing said infed measured values and said particle numbers associated therewith in order to carry out said step of utilizing said separation threshold values and said at least one separation threshold value determined on the basis of said selected characteristic predetermined difference quotient for determining said particle distribution as a function of said predetermined particle parameter.

7. The method as defined in claim 1, further including:

analyzing, as said particles dispersed in a fluid, blood cells dispersed in a blood sample liquid;

measuring as said measured values of said predetermined particle parameter and said number of particles associated with said measured value, the size and the number of blood cells contained in said blood sample liquid constituting said particle containing fluid; and said step of utilizing said separation threshold values and said at least one separation threshold value determined on the basis of said at least one selected characteristic predetermined difference quotient for determining said particle distribution entailing the step of determining, said particle distribution as a function of said predetermined particle parameter, the concentrations of lymphocyte cells and granulocyte cells in said blood sample.

8. The method as defined in claim 1, wherein:

said step of determining said at least one selected characteristic predetermined difference quotient associated with said at least one particle population minimum entails determining said at least one selected characteristic predetermined difference quotient in accordance with the relationship:

$$Q_x(j,k)_{res} = \frac{\text{Min.}(x) - \text{Min.}(j)}{\text{Max.}(k) - \text{Min.}(j)}$$

wherein:

$Q_x(j,k)_{res}$ is an x-th selected characteristic predetermined difference quotient determined in said individual histograms containing a sufficiently resolved particle population maximum Max.k, a sufficiently resolved particle population minimum Min.j and a sufficiently resolved particle population minimum Min.x which corresponds to said at least one insufficiently resolved particle population minimum in said selected histograms;

x is an index relating said selected characteristic predetermined difference quotient $Q_x(j,k)_{res}$ to said predetermined number of particle population minima in said individual histograms;

Min.(x) is said measured value of said predetermined particle parameter at the location of said particle population minimum Min.x of said predetermined number of particle population minima in said individual histograms and which particle population minimum Min.x corresponds to said at least one insufficiently resolved particle population minimum in said selected histograms;

Min.(j) is the measured value of said predetermined particle parameter in said individual histograms at the location of said sufficiently resolved particle population minimum Min.j which corresponds to a sufficiently resolved particle population minimum in said selected histograms;

j is an index relating said sufficiently resolved particle population minimum Min.j to said predetermined number of particle population minima in said individual histograms;

Max.(k) is the measured value of said predetermined particle parameter in said individual histograms at the location of said sufficiently resolved particle population maximum Max.k which is associated with said particle population minimum Min.x and corresponds to a particle population maximum in said selected histograms; and k is an index relating said sufficiently resolved particle population maximum Max.k to said predetermined number of particle population maxima in said individual histograms.

9. The method as defined in claim 8, wherein:

said step of determining said at least one separation threshold value associated with said at least one insufficiently resolved particle population minimum in said selected histograms on the basis of said at least one selected characteristic predetermined difference quotient includes the step of determining said at least one separation threshold value associated with said insufficiently resolved particle population minimum in accordance with the relationship:

$S_x(j,k)_{unres} =$
$(\text{Max.}(k) - \text{Min.}(j))_{unres} \cdot Q_x(j,k)_{res} + \text{Min.}(j)_{unres}$ wherein:

$S_x(j,k)_{unres}$ constitutes an x-th separation threshold value which corresponds to said insufficiently resolved particle population minimum Min.x in said selected histograms and which is to be determined on the basis of said x-th selected characteristic predetermined different quotient $Q_x(j,k)_{res}$;

x is an index relating said x-th separation threshold value to said predetermined number of particle population minima in said individual histograms;

Max.(k) is the measured value of said predetermined particle parameter in said selected histograms at the location of said sufficiently resolved particle population maximum Max.k which is associated with said insufficiently resolved particle population minimum Min.x in said selected histograms;

k is said index relating said sufficiently resolved particular population maximum Max.k to said predetermined number of particle population maxima in said individual histograms;

Min.(j) is the measured value of said predetermined particle parameter in said selected histograms at the location of said sufficiently resolved particle population minimum Min.j in said selected histograms;

j is said index relating said sufficiently resolved particle population minimum Min.j to said predetermined number of particle population minima in said individual histograms; and $Q_x(j,k)_{res}$ is said x-th selected characteristic predetermined different quotient determined in said individual histograms containing said sufficiently resolved particle population maximum Max.k, said sufficiently resolved particle population minimum Min.j and said sufficiently resolved particle population minimum Min.x which corresponds to said at least one insufficiently resolved particle population minimum in said selected histograms.

10. The method as defined in claim 8, further including the steps of:
    determining said at least one selected characteristic predetermined difference quotient for a predetermined number of samples of said particle containing fluid;
    forming and storing at least one mean value of said at least one selected characteristic predetermined difference quotient determined for said predetermined number of samples of said particle containing fluid;
    verifying said at least one mean value of said at least one selected characteristic predetermined difference quotient in relation to said at least one associated sufficiently resolved particle population minimum in at least one histogram of said predetermined number of histograms; and
    adaptively optimizing said at least one mean value of said at least one selected characteristic predetermined difference quotient to said at least one associated sufficiently resolved particle population minimum in said at least one histogram of said predetermined number of histograms in the event of insufficient verification.

11. A method of determining separation threshold values for particle analysis of a sample of a particle containing fluid, especially a liquid containing a blood sample, comprising the steps of:
    determining measured values of a predetermined particle parameter and the number of particles having said measured values and contained in individual samples of a predetermined number of samples of a particle containing fluid;
    arranging said measured values and said number of particles in the form of individual histograms containing at least two particle population maxima and at least two particle population minima;
    adaptively determining at least one of said at least two particle population minima;
    determining a predetermined number of characteristic predetermined difference quotients for said individual histograms on the basis of associated ones of said at least two particle population maxima and said at least two particle population minima;
    ordering and storing at least one selected characteristic predetermined difference quotient of said predetermined number of characteristic predetermined difference quotients and forming at least one mean value of said at least one selected characteristic predetermined difference quotient which is related to at least one insufficiently defined separation threshold value associated with at least one insufficiently resolved particle population minimum of said at least two particle population minima in selected ones of said individual histograms;
    selecting at least one appropriate selected characteristic predetermined difference quotient for fixing said at least one insufficiently defined separation threshold value in said selected individual histograms;
    determining the presence of said at least one appropriate selected characteristic predetermined difference quotient and, in the absence of such at least one appropriate selected characteristic predetermined difference quotient, storing related ones of said selected individual histograms containing said at least one insufficiently resolved particle population minimum;
    determining said at least one insufficiently defined separation threshold value on the basis of selected ones of said at least two particle population maxima, said at least two particle population minima and said at least one appropriate selected characteristic predetermined difference quotient;
    presetting boundary conditions for said at least one thus determined separation threshold value;
    during said step of determining said at least one insufficiently defined separation threshold value, checking the at least one thus determined separation threshold value for consistency with said preset boundary condition;
    using said at least one determined and checked separation threshold value for determining related values of said predetermined particle parameter; and
    detecting in said individual histograms, non-analyzable histograms which cannot be analyzed due to the presence of insufficiently defined separation threshold values and signalling the presence of such non-analyzable histograms.

12. An apparatus for analyzing particles dispersed in a fluid, comprising:
    a measuring device measuring values of a predetermined particle parameter and the number of particles associated with said measured values and contained in individual samples of a predetermined number of samples of a particle containing fluid;
    evaluating means connected to said measuring device and containing:
    arranging means connected to said measuring device and for arranging said measured values of said predetermined particle parameter and said number of particles associated with said measured values and contained in said individual samples, in the form of individual histograms of a predetermined number of histograms related to said predetermined number of samples of said particle containing fluid, each said individual histogram containing a predetermined number of particle population maxima and a predetermined number of particle population minima;
    means connected with said arranging means and for determining, from said individual histograms, a predetermined number of separation threshold values associated with sufficiently resolved ones of said predetermined number of particle population minima;
    detection connected with said arranging means and said determining means, for detecting in said predetermined number of histograms, selected histograms containing at least one insufficiently resolved particle population minimum unsuitable for directly determining at least one separation threshold value;
    means associated with said arranging means and for determining, from said individual histograms, at least one selected characteristic predetermined difference quotient associated with at least one sufficiently resolved particle population minimum of said predetermined number of particle population minima and which at least one sufficiently resolved particle population minimum corresponds to said at least one, insufficiently resolved particle population minimum from said selected histograms;

said determining means further determining, in said selected histograms and on the basis of said at least one selected predetermined difference quotient, said at least one separation threshold value associated with said at least one insufficiently resolved particle population minimum; and said evaluating means utilizing said predetermined number of separation threshold values and said at least one separation threshold value determined on the basis of said at least one selected characteristic predetermined difference quotient for determining the particle distribution as a function of said predetermined particle parameter in each said individual sample of said predetermined number of samples of said particle containing fluid.

13. The apparatus as defined in claim 12, further including:

first storage means constituting a component of said arranging means for arranging said measured values of said predetermined particle parameter and said number of particles associated with said measured values and contained in said individual samples in the form of said individual histograms;

said first storage means being connected to said measuring device;

said first storage means containing a predetermined number of storage channels; and each one of said predetermined number of storage channels storing predetermined measured values of said predetermined particle parameter under associated storage channel addresses.

14. The apparatus as defined in claim 13, further including:

a first computing section constituting a further component of said arranging means and connected with said first storage means;

said first computing section fixing selected ones of said associated storage channel addresses; and said fixed selected storage channel addresses being associated with said predetermined number of particle population maxima and said predetermined number of particle population minima in said individual histograms.

15. The apparatus as defined in claim 14, wherein:

said first computing section containing said detection means for detecting, in said predetermined number of histograms, said selected histograms containing at least one insufficiently resolved particle population minimum unsuited for directly determining said at least one separation threshold value.

16. The apparatus as defined in claim 15, further including:

a third computing section constituting said means for determining said at least one selected characteristic predetermined difference quotient associated with said at least one sufficiently resolved particle population minimum in said individual histograms; and said third computing section interconnecting said first computing section and said second computing section.

17. The apparatus as defined in claim 16, further including:

a fourth computing section constituting said means for determining, on the basis of said at least one selected characteristic predetermined difference quotient, said at least one separation threshold value associated with said at least one insufficiently resolved particle population minimum; and said fourth computing section interconnecting said second computing section and said third computing section.

18. The apparatus as defined in claim 17, wherein:

said fourth computing section contains means for fixing boundary conditions for the at least one separation threshold value determined on the basis of said at least one selected characteristic predetermined difference quotient and associated with said at least one insufficiently resolved particle population minimum in said selected histograms; and said fourth computing section further containing means for determining whether said at least one separation threshold value satisfies said fixed boundary conditions.

19. The apparatus as defined in claim 16, further including:

second storage means interconnected between said second computing section and said third computing section;

said second storage means storing said at least one selected characteristic predetermined difference quotient received from said third computing section; and said second storage means forming at least one mean value of said at least one selected characteristic predetermined difference quotient stored in said second storage means.

20. The apparatus as defined in claim 19, further including:

verifying means for verifying said at least one means value of said at least one selected characteristic predetermined difference quotient stored in said second storage means;

said verifying means verifying said at least one means value in relation to at least one associated sufficiently resolved particle population minimum in at least one histogram of said predetermined number of histograms;

adaptive optimizing means for adaptively optimizing said at least one means value of said at least one selected characteristic predetermined different quotient with respect to said at least one associated sufficiently resolved particle population minimum in said at least one histogram in the event of insufficient verification; and said verifying means and said adaptive optimizing means being associated with said third computing section.

21. The apparatus as defined in claim 16, further including:

third storage means connected with said third computing section; and said third storage means intermittently storing said selected histograms containing said at least one insufficiently resolved particle population minimum, in the absence of a related selected characteristic predetermined difference quotient.

22. The apparatus as defined in claim 16, wherein:

said third computing section determining said at least one characteristic predetermined difference quotient in accordance with the relationship:

$$Q_x(j,k)_{res} = \frac{\text{Min.}(x) - \text{Min.}(j)}{\text{Max.}(k) - \text{Min.}(j)}$$

wherein $Q_x(j,k)_{res}$ is an x-th selected characteristic predetermined difference quotient determined in said individual histograms containing a sufficiently resolved particle population maximum Max.k, a sufficiently resolved particle population minimum Min.j and a sufficiently resolved particle population minimum Min.x which corresponds to said at least one insufficiently resolved particle population minimum in said selected histograms;

x is an index relating said selected characteristic predetermined difference quotient $Q_x(j,k)_{res}$ to said predetermined number of particle population minima in said individual histograms;

Min.(x) is said measured value of said predetermined particle parameter at the location of said particle population minimum Min.x of said predetermined number of particle population minima in said individual histograms and which particle population minimum Min.x corresponds to said at least one insufficiently resolved particle population minimum in said selected histograms;

Min.(j) is the measured value of said predetermined particle parameter in said individual histograms at the location of said sufficiently resolved particle population minimum Min.j which corresponds to a sufficiently resolved particle population minimum in said selected histograms;

j is an index relating said sufficiently resolved particle population minimum Min.j to said predetermined number of particle population minima in said individual histograms;

Max.(k) is the measured value of said predetermined particle parameter in said individual histograms at the location of said sufficiently resolved particle population maximum Max.k which is associated with said particle population minimum Min.x and corresponds to a particle population maximum in said selected histograms; and k is an index relating said sufficiently resolved particle population maximum Max.k to said predetermined number of particle population maxima in said individual histograms.

23. The apparatus as defined in claim 22, further including:

a fourth computing section constituting said means for determining, on the basis of said at least one selected characteristic predetermined difference quotient, said at least one separation threshold value associated with said at least one insufficiently resolved particle population minimum;

said fourth computing section interconnecting said second computing section and said third computing section; and said fourth computing section determining said at least one separation threshold value associated with said at least one insufficiently resolved particle population minimum Min.x in said selected histograms in accordance with the relationship:

$S_x(j,k)_{unres} = (Max.(k) - Min.(j))_{unres} \cdot Q_x(j,k)_{res} + Min.(j)_{unres}$ wherein:

$S_x(j,k)_{unres}$ constitutes an x-th separation threshold value which corresponds to said insufficiently resolved particle population minimum Min.x in said selected histograms and which is to be determined on the basis of said x-th selected characteristic predetermined difference quotient $Q_x(j,k)_{res}$;

x is an index relating said x-th separation threshold value to said predetermined number of particle population minima in said individual histograms;

Max.(k) is the measured value of said predetermined particle parameter in said selected histograms at the location of said sufficiently resolved particle population maximum Max.k which is associated with said insufficiently resolved particle population minimum Min.x in said selected histograms;

k is said index relating said sufficiently resolved particle population Max.k to said predetermined number of particle population maxima in said individual histograms;

Min.(j) is the measured value of said predetermined particle parameter in said selected histograms at the location of said sufficiently resolved particle population minimum Min.j in said selected histograms;

j is an index relating said sufficiently resolved particle population minimum Min.j to said predetermined number of particle population minima in said individual histograms; and $Q_x(j,k)_{res}$ is said x-th selected characteristic predetermined difference quotient determined in said individual histograms containing said sufficiently resolved particle population maximum Max.k, said sufficiently resolved particle population minimum Min.j and said sufficiently resolved particle population minimum Min.x which corresponds to said at least one insufficiently resolved particle population minimum in said selected histograms.

24. The apparatus as defined in claim 14, further including:

a second computing section constituting said means for determining, from said individual histograms, said predetermined number of separation threshold values associated with said sufficiently resolved particle population minima;

said second computing section being connected with said first computing section and said measuring device; and said second computing section further containing control signal generating means for supplying control signals controlling the operation of said measuring device.

25. The apparatus as defined in claim 24, further including:

an output unit connected with said second computing section;

said second computing section containing control signal generating means generating at least one control signal for controlling the operation of said output unit; and said at least one control signal corresponding to said at least one separation threshold value associated with said at least one insufficiently resolved particle population minimum.

26. The apparatus as defined in claim 12, wherein:

said measuring device constitutes a blood analyzer measuring, as said predetermined particle parameter, the size and counting the number of blood cells associated with the measured sizes and contained in individual samples of a predetermined number of samples of a liquid containing blood samples; and said evaluating means determining, as said particle distribution as a function of said predetermined particle parameter, the concentrations of lymphocyte cells and granulocyte cells in said individual samples of said liquid containing blood samples.

27. An apparatus for determining separation threshold values for particle analysis of a sample of particle containing fluid, especially a liquid containing a blood sample, comprising:

at least one measuring device for measuring measured values of a predetermined parameter of particles and the number of particles associated with said measured values and contained in individual samples of said particle containing fluid;

first storage means connected to said measuring device and containing at least one storage channel for storing at predetermined storage addresses associated digitized measured values and the time of occurrence of said measured values;

a first computing section connected to said first storage means for processing a predetermined number of said digitized measured values in order to form individual histograms which are associated with said individual samples of said particle containing fluid;

said first computing section processing said predetermined number of digitized measured values for reducing quantization errors, for first and higher order smoothing, selecting predetermined regions from said individual histograms by fixing selected ones of said predetermined number of storage addresses for determining a predetermined number of particle population maxima and a predetermined number of particle population minima from said individual histograms, and checking the thus determined predetermined number of particle population maxima and particle population minima;

a second computing section associated with said first computing section and utilizing said predetermined number of particle population minima for particle analysis by integration;

said second computing section initiating particle analysis of each individual sample of said particle containing fluid;

said second computing section containing control signal generating means generating control signals controlling the operation of said at least one measuring device;

a third computing section interconnecting said first computing section and said second computing section and containing means for determining a predetermined number of characteristic predetermined difference quotients associated with said predetermined number of particle population minima in said individual histograms;

said third computing section further containing selecting means for selecting at least one selected characteristic predetermined difference quotient which is related to at least one insufficiently defined separation threshold value to be fixed and associated with at least one insufficiently resolved particle population minimum in selected ones of said individual histograms;

said third computing section further containing means for determining the presence of said at least one selected characteristic predetermined difference quotient;

said third computing section containing storing means for storing individual ones of said selected histograms during the absence of said at least one selected characteristic predetermined difference quotient;

second storage means interconnected between said first, second and third computing sections;

said second storage means ordering and storing said at least one selected characteristic predetermined difference quotient which is related to said at least one insufficiently defined separation threshold value;

said second storage means containing means for forming at least one mean value of said at least one selected characteristic predetermined difference quotient;

a fourth computing section interconnecting said second computing section and said third computing section;

said fourth computing section containing means for determining said at least one insufficiently defined separation threshold value on the basis of said at least one selected characteristic predetermined difference quotient;

said fourth computing section further containing means for fixing boundary conditions for said at least one insufficiently defined separation threshold value;

said fourth computing section further containing means for checking whether said at least one threshold value which has been determined on the basis of said at least one selected characteristic predetermined difference quotient, satisfies said fixed boundary conditions;

third storage means connected to said third computing section and constituting said storing means for storing individual histograms during the absence of said at least one selected characteristic predetermined difference quotient; and said third storage means containing means for infeeding said stored individual histograms at a later time of the operation after said selected characteristic predetermined difference quotient has been determined.

* * * * *